United States Patent
Chuang et al.

(10) Patent No.: US 10,175,176 B2
(45) Date of Patent: Jan. 8, 2019

(54) METHOD OF EVALUATING CHARACTERISTICS OF ION IMPLANTED SAMPLE

(71) Applicant: TAIWAN SEMICONDUCTOR MANUFACTURING CO., LTD., Hsinchu (TW)

(72) Inventors: Kuo-Sheng Chuang, Hsinchu (TW); You-Hua Chou, Hsinchu (TW)

(73) Assignee: TAIWAN SEMICONDUCTOR MANUFACTURING COMPANY LIMITED, Hsinchu (TW)

( * ) Notice: Subject to any disclaimer, the term of this patent is extended or adjusted under 35 U.S.C. 154(b) by 183 days.

(21) Appl. No.: 15/158,531

(22) Filed: May 18, 2016

(65) Prior Publication Data

US 2017/0138863 A1 May 18, 2017

Related U.S. Application Data

(60) Provisional application No. 62/256,964, filed on Nov. 18, 2015.

(51) Int. Cl.
*G01N 21/78* (2006.01)
*H01L 21/66* (2006.01)
(Continued)

(52) U.S. Cl.
CPC .......... *G01N 21/78* (2013.01); *G01N 21/63* (2013.01); *H01L 21/265* (2013.01);
(Continued)

(58) Field of Classification Search
CPC .. G01N 2021/634; G01N 21/78; G01N 21/63; H01L 21/265; H01L 22/10; H01L 22/12
See application file for complete search history.

(56) References Cited

U.S. PATENT DOCUMENTS 5,773,316 A 6/1998 Kurosaki et al.
6,151,119 A 11/2000 Campion et al.
(Continued)

FOREIGN PATENT DOCUMENTS

JP 04005816 A 1/1992
JP 2004031465 A 1/2004
(Continued)

OTHER PUBLICATIONS

PD Townsend et al., "Optical Effect of Ion Implantation" Reports on Progress in Physics, vol. 50, No. 5, May, 1987.
(Continued)

*Primary Examiner* — Hina F Ayub
*Assistant Examiner* — Amanda Merlino
(74) *Attorney, Agent, or Firm* — Cooper Legal Group, LLC

(57) ABSTRACT

A method of evaluating characteristics of a work piece includes forming a photosensitive layer on the work piece. Then an ion implantation is performed on the work piece. The work piece is radiated, and an optical intensity of the photosensitive material on the work piece is calculated. The ion implantation pattern is evaluated according to the optical intensity. A chemical structure of the photosensitive material is changed upon the ion implantation. The work piece is recovered by reversing the chemical structure of the photosensitive material or removing the ion interrupted photosensitive material by chemicals.

20 Claims, 4 Drawing Sheets

(51) Int. Cl.
*H01L 21/268* (2006.01)
*H01L 21/265* (2006.01)
*H01L 21/3105* (2006.01)
*G01N 21/63* (2006.01)

(52) U.S. Cl.
CPC ...... *H01L 21/268* (2013.01); *H01L 21/31058* (2013.01); *H01L 22/10* (2013.01); *G01N 2021/634* (2013.01); *H01L 22/12* (2013.01)

(56) References Cited

U.S. PATENT DOCUMENTS

| | | | |
|---|---|---|---|
| 6,620,632 B2 * | 9/2003 | Koveshnikov | H01L 22/12 257/E21.318 |
| 2002/0080356 A1 | 6/2002 | McMillen et al. | |
| 2008/0128621 A1 | 6/2008 | Berry | |

FOREIGN PATENT DOCUMENTS

| | | |
|---|---|---|
| KR | 10-0255961 A | 5/2000 |
| KR | 10-2001-0032343 A | 4/2001 |
| TW | 201348829 A | 12/2013 |

OTHER PUBLICATIONS

Corresponding Korean Application Office Action dated Oct. 18, 2017 (8 pgs).
Corresponding Taiwan Application Office Action dated Sep. 7, 2017 (12 pgs).
Wiki; www.twwiki.com/wiki Sep. 25, 2013 (6 pgs).

* cited by examiner

METHOD OF EVALUATING CHARACTERISTICS OF ION IMPLANTED SAMPLE

PRIORITY CLAIM AND CROSS-REFERENCE

This application claims priority to U.S. Provisional Application Ser. No. 62/256,964, filed Nov. 18, 2015, which is herein incorporated by reference.

BACKGROUND

Ion implantation is used for the incorporation of dopant impurities into semiconductor wafers for the formation of semiconductor devices such as field effect transistors (FETs) and bipolar junction transistors (BJTs). A focused beam of ions is generated in an apparatus called an ion implanter. The beam is produced by ionising molecules or atms in a source gas and then electrostatically collimating, filtering to exclude unwanted ions and focusing the beam on the target wafer surface. Ideally, the treated wafer surface has a uniform radial density and spot size generated by the focused beam. The entire wafer surface is exposed to the beam, and ions are driven into the wafer surface. The depth of how far the ion travels is dependent upon their energy within the beam. That is, ion density in the beam and time of exposure have great effect to the pattern of dosage implantation.

However, the actual density of ions is not uniform across the focused beam that forms the pattern. Typically, the dosage of the resultant implant is greater at the center of the scan line than at the edges. The effects of variations in the dopant profile is more complicated than expected, but the dopant profile is significant because the planar dimensions of semiconductor device is ever decreasing. This is of particular importance for ion implantations which are related to device performance, for example, threshold voltage adjustment of metal oxide semiconductor field effect transistors (MOSFETs).

The dopant profile is complex and not as predictable as would be expected from periodic behaviour. It is therefore imperative to devise a method, not only to monitor the dopant distribution for process control but also to enable a better understanding of the mechanisms behind.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
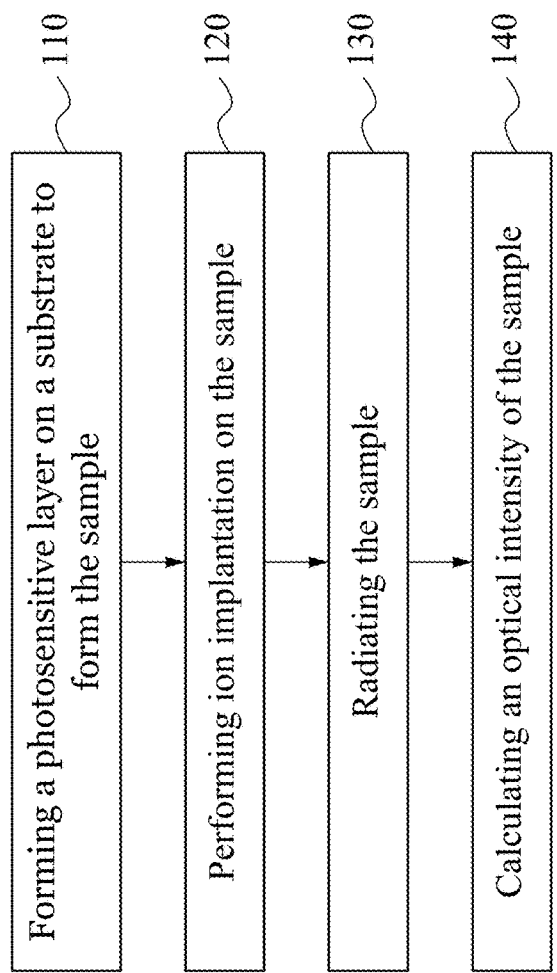
FIG. 1 is a flow chart showing a method of evaluating characteristics of a sample after ion implantation in accordance with some embodiments of the instant disclosure.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Current method for monitoring or measuring the uniformity of ion implant dosage is limited to the measurement of sheet resistance, capacitance voltage measurements, thermal wave measurements, secondary ion mass spectrometry and low energy electron induced X-ray emission spectrometry. In the sheet resistance measurement, a thermal annealing which repairs crystal damage and activates dopant occurs after ion implantation. The high temperature of thermal annealing which can reach to 900° C. facilitates ion diffusion and sheet resistance decreases. This additional thermal annealing treatment adds another variation to the measurement and probably error as well. Incompleteness of anneal appears when non-uniformities in structural damage caused by ion implantation along with malfunctioning of the rapid thermal anneal process results in residual structural damage areas on the surface of the work piece. A sheet resistance map of a wafer work piece which is subjected to ion implantation by, for example, boron ions is determined by the four-probe method of resistivity measurement. Low sheet resistance readout may be caused not by an increased dose of dopant, but rather it is due to planar channelling. The contact resistance leads to unreliable measurement results. The pure silicon wafer cannot be recycled after sheet resistance measurement, and the entire process consumes a considerable period of time because of the involvement of thermal annealing and probes set up.

Thermal wave and plasma wave monitoring systems typically are based on the detection of changes in intensity of a probe beam reflected off the surface of the work piece. Changes in the reflectivity of the surface are caused by thermal and plasma waves arising as a result of the absorption of an intensity-modulated pump beam directed at or near the same area on the surface as the probe beam. To monitor the surface changes, a probe laser is used to direct a probe beam at a portion of the work piece that is excited by the pump laser. As the pump laser is modulated, the localized excitation and subsequent relaxation creates a train of termal and plasma waves within the work piece. These waves reflect and scatter off various features and interact with various regions within the work piece in a way that alters the flow of heat and/or plasma from the pump beam spot. The work piece reflects the probe beam and a photodetector records the intensity of the reflected probe beam. The output signal from the photodetector is filtered to isolate the changes that are synchronous with the pump beam modulation. The detector generates separate outputs that can be supplied to a processor and used to calculate amplitude and phase of the modulated signal. The amplitude and phase values are used to deduce physical characteristics of the work piece. However, thermal wave measurement is not suitable for detection in high energy or high dosage ion implantation because the lattice has to be exited in the detection process, and the lattice vibration change is captured by the photodetector. Thermal wave measurement has low rate in repeatability and reproducibility due to crystal restructuring effect. Work pieces with certain dimension, for example, higher than 450 mm, cannot fit into a conventional thermal wave measurement system. Recycling of the work piece can be costly because of the front surface damage in the measurement process. Secondary ion mass spectrometry bombards the surface of the work piece, and atom splashing at a single point is measured to be translated into physical characteristics of the ion implantation result on the work piece. Secondary ion mass spectrometry is relatively expensive and the process time is slow. Low energy electron induced X-ray emission spectrometry can only be applied to work pieces having ultra shallow implant at high dosage, and therefore its application is strictly narrow.

The understanding and prediction of ion implantation map is strongly related to the device performance. A method capable of measuring implanted wafer surfaces with fine enough resolution to reveal these dopant variations is provided. It is achieved by the employment of photosensitive materials, changing structure upon stimuli. The stimuli may be ions or other higher energy source, for example, UV or photon, which make transparency of the work piece an index of ion implantation. Depending on the choice of ion, ion energy and ion dose results in various degree of luminescence and generates implantation map including optical absorption or reflecting detect.

Turning now to FIG. 1, illustrated is an embodiment of a method 100 of evaluating characteristics of an ion implanted work piece. Embodiments of the method 100 shown in FIG. 1 are further illustrated in the schematic diagrams of FIGS. 2A through 2C, and reference should be made to these figures as called out in the text below.

Figure 2B:
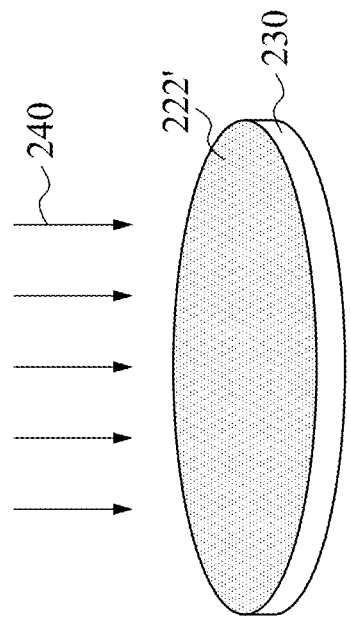
FIGS. 2A-2C are schematic diagrams showing a method of evaluating characteristics of a sample after ion implantation in accordance with some embodiments of the instant disclosure.
Figure 2A:
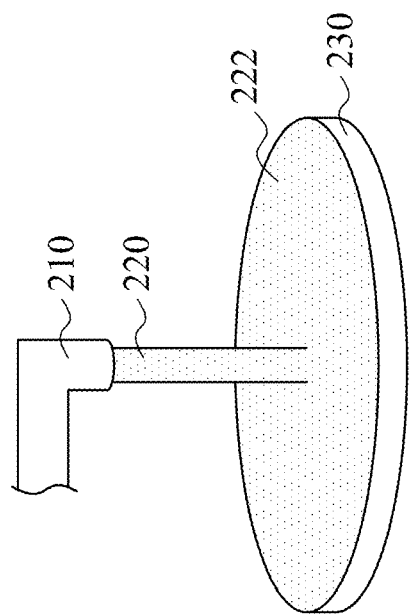

As set forth in operation 110 in FIG. 1, a photosensitive material is dispensed on a substrate. This is illustrated in FIG. 2A, which shows a substrate 230 under a running dispenser 210. The substrate 230 is permeable to light having wavelength ranging from approximately 380 nm to 700 nm. This small portion of electromagnetic radiation is usually referred to as visible light. Visible light is perceptible to naked human eyes. Violet has the shortest wavelength, at around 380 nm, and red has the longest wavelength, at around 700 nm. The transmission of light through the substrate 230 is related to the interpretation of the ion implantation map. More specifically, the transparency of the substrate 230 is an indicator of the ion implantation map. The substrate 230 may be a silicon wafer, silicon on insulation (SOI) wafer, GaAs wafer, sapphire wafer or a glass substrate. In some embodiments, the substrate 230 is a glass substrate (wafer), allowing nearly full range of visible light to travel through. The substrate 230 may be unimplanted to start with or recycled from a previous test process. A thickness of the substrate 230 is measured of approximately 500 μm to 1000 μm.

A photosensitive material 220, also known as a photochromic material 220, is released from the dispenser 210 onto the surface of the substrate 230. The deposition method of the photosensitive material 220 may vary, for example, by chemical vapour deposition or physical vapour deposition, and the instant disclosure is not limited thereto. The photosensitive material 220 may come in the form of gas, vapour or liquid depending on the property of the photosensitive material 220. As shown in FIG. 2A, the photosensitive material 220 forms a film 222 on the front surface of substrate 230 and entirely blankets the front surface of the substrate 230 with a photosensitive layer 222. The back surface of the substrate 230 is clear of any coverage of the photosensitive material 220. The photosensitive layer 222 is polished to ensure a flat and even photosensitive material 220 distribution. During the time of photosensitive layer 222 formation and before the work piece is ion implanted, the process is conducted under room temperature and any source containing electromagnetic radiation should be blocked out. The photosensitive material 220 contains chemicals that are highly sensitive to high energy particles. If the photosensitive material 220 undergoes unwanted exposure or excitement before ion implantation, chemical structure of the photosensitive material 220 is likely to be altered, resulting in false readout. The ambient temperature is carefully controlled because some of the photosensitive material 220 is not only sensitive to high energy particles but also temperature. Similar to unwanted exposure, temperature fluctuation may cause chemical structure alternation of the photosensitive material 220 not resulting from ion implantation. The thickness of the photosensitive layer 220 ranges from approximately 1000 Å to 8000 Å. The photosensitive material 220 forms a photosensitive layer 222 on the substrate 230, and an unimplanted work piece is completed.

A material of the photosensitive layer 222 may include, for example, spiropyrans, spirooxazines, diarylethenes, azobenzenes, poly[N,N'-(p,p'-oxydiphenylene)pyromellitimide (Kapton H), 4-N, N-dimethylamino-4-N/-methyl-stilbazolium tosylate (DAST), AgBr and a combination thereof. A photosensitive material or a photochromic compound can be considered as a reversible dye under photochemical control. Photochromism can be defined as a reversible transformation of a chemical species, induced in one or both directions by electromagnetic radiation, between two states having observable light absorptions in different regions of the spectrum. When the chemical species changes between a first and a second states, the second state has at least one absorption band appearing at longer wavelength than the absorption bands of the first state, vice versa. A lot of photochromic systems are based on unimolecular reactions.

Reversibility is the main criterion for photochromism. The back reaction from the second state to the first state may occur predominately by a thermal mechanism. For these systems, the thermally driven back reaction may be accompanied by one that is photochemically driven, but the thermal reaction normally predominates. In other systems (e.g., fulgides or arylethenes), the photochemically induced forms, i.e., second state, are thermally stable. For such systems, the back reactions are predominately photochemical. The photochromic transformation and the observed spectral changes or changes in physical or chemical behaviour are related to the modification of the geometry of the system and its electronic distribution. The importance of the medium in which the photochromic compound is incorporated can strongly influence or control the kinetics of the thermal back reaction. In the instant disclosure, the medium will be the ion used in the ion implantation. When ion implantation takes place, the colour of the species formed in the forward photochemical reaction and other properties of the photochromic material collectively provide another approach to interpret the result of the treatment.

There are two general types of photochromic applications. The first one is application directly dependent upon the colour change caused by the differences between the molecular and electronic structures of the species and their corresponding absorption or emission spectra. A second type application is dependent upon changes in physical or chemical properties that accompany the more easily observed colour change during the photochromic reaction. Examples of such properties are conductivity, refractive index, electrical moment, dielectric constant, chelate formation, ion dissociation, phase transitions, solubility and viscosity. Certain physical changes that occur when the photochromic entity is chemically attached to the macromolecular backbone of polymers are of special interest.

Upon excitement, transformation occurs from the first state to the second state. For example, spirooxazines changes from leuco form to coloured form, where the spiro-carbon and oxygen bond breaks and the ring opens. In the case of diarylethenes, the open form is nearly transparent, while in the closed form the compound gives a colour. Azobenzenes changes between trans- and cis-forms, but the transformation is not accompanied by a distinct colour change owing to the overlapping of the absorption bands of the E- and Z-isomers. Instead, the reversible geometrical photoisomerization gives rise to the versatile photofunctionality of polymeric materials incorporating azobenzenes. The alteration of chemical as well as physical properties induced by changes in the molecular structure of the azobenzns contributes to notable spectral shifting of other compounds. Kapton H is brown and transparent in the first state. When energetic $N^{2+}$ ions are implanted (i.e., exciting the chemical species), Kapton H turns into black. The shade of black changes along with the increase of $N^{2+}$ dose. By adding more energetic $N^{2+}$, black transforms into greyish silver with a remarkable metallic luster. In the second type of application, DAST changes its refractive index between the first and second states. DAST shows lower refractive index, a reduction of 0.2 at wavelengths of 633 nm (red light), when $H^+$ ions are implanted. This refractive reduction is a useful indicator of mapping ion implantation.

Returning to FIG. 1, as set forth in operation 120, an ion implantation is performed on the work piece. This is illustrated in FIG. 2B, where the photosensitive layer 222 is excited by ion beams 240 to an excited state of photosensitive layer 222'. When ions are implanted into silicon, they damage the crystalline lattice structure. This damage, in turn, changes, for example, the index of refraction and the absorption coefficient of the silicon. For the work piece having the photosensitive layer on the surface, this will show up as a change in the transmission spectrum. The wavelengths of maximum and minimum transmission will be altered. The property of the photochromic material changes, for example, ring opening or trans-cis transformation, according to the implanted ion dose and energy, and these facts forms the basis of these transmission studies.

Figure 2C:
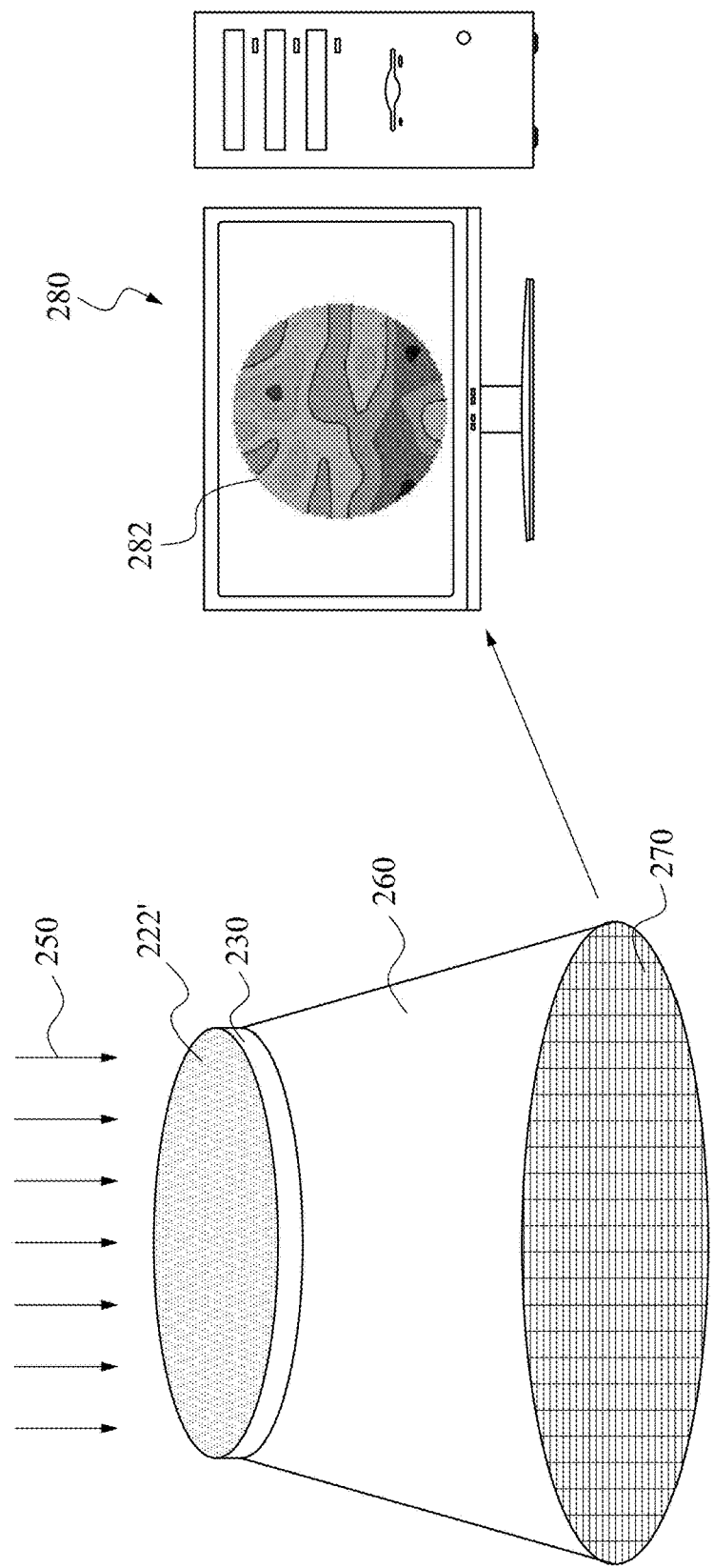

Returning to FIG. 1, as set forth in operation 130, the work piece is radiated under standard illumination source. This is illustrated in FIG. 2C, where a light source 250 shines on the ion implanted photosensitive layer 222'.

After ion implantation, the ion implantation result is translated to an ion implantation map 282 through a measurement system. The measurement system includes a light source 250, a light shelter 260, a meter matrix 270 and a process unit 280. The light source 250 is a standard illumination source, emitting light on the implanted photosensitive layer 222' of the substrate 230. The coverage of the light source 250 is greater than the surface area of the photosensitive layer 222'. When the light source 250 is lit, the implanted photosensitive layer 222' is completely immersed in the light casting from the top. The light source is positioned at an angle that allows sufficient and evenly distributed light coverage on the substrate 230. The light shelter 260 has a top platform for retaining the work piece atop. The platform accommodates the work piece in between the light shelter 260 and the light source 250. The platform has a dimension equal to or larger than the substrate 230 and is made of a material that is permeable to visible light. The top of the light shelter 260 is capped by the platform, and the bottom of the light shelter 260 is sealed by the meter matrix 270. The wall of light shelter blocks out any visible light interference from the ambience and allows only the light coming through the photosensitive layer 222'. The meter matrix 270 is placed in parallel to the platform and has a dimension equal to or larger than the platform. Referring to FIG. 2C, the meter matrix 270 has a larger diameter of the platform, and the light shelter 260 encloses the area in between the meter matrix 270 and the light shelter, forming a tapered outline. The geometric configuration of the platform, meter matrix 270 and light shelter is not limited to the diagram. Any geometric configuration is acceptable as the work piece can be securely retained, and its projection will be fully received by the meter matrix 270.

Returning to FIG. 1, as set forth in operation 140, an optical intensity of the photosensitive material on the work piece is calculated. The meter matrix 270 is composed of a plurality of cells that are sensitive to electromagnetic radiation. The meter matrix 270 is coupled to a processing unit 280, and the data received by the meter matrix 270 will be translated into ion implantation map 282. The spatially averaged measurements of the optical intensity can be repeated at specified cell location and calculated. The number and position of these locations can be configurable. As a result, a map or array of intensity value across the substrate surface can be generated, which give a measure of the implantation uniformity of the photosensitive layer 222'. When the light source 250 sheds on the work piece, the entire surface of the substrate 230 is in the light coverage. The light travels through the photosensitive layer 222', the substrate 230 and the platform and enters the space enclosed by the light shelter 260. As previously discussed, the substrate 230 is permeable to visible light having wavelength ranging between approximately 380 nm and 700 nm. The same property applies to the platform, such that any electromagnetic radiation that is allowed to go through the substrate 230 can pass through the platform. The light beams bearing different intensity hit the cells of the meter matrix, and a projection of the work piece is virtually printed on the meter matrix 270.

The meter matrix 270 is coupled to the processing unit 280 and transfers the data to the processing unit 280 for further manipulation. The spectral shift resulting from ion implantation is recorded and calculated by the processing unit 280, and a map of the ion implantation 282 can be obtained. The ion implantation map 282 reflects the ion distribution on the photosensitive layer 222'. Take energetic $N^{2+}$ implantation on Kapton H layer for example. Before ion implantation, the photosensitive layer 222 containing Kapton H is brown and transparent. Once $N^{2+}$ implantation is performed, different shades of grey and black appears. Areas showing greyish silver indicate a heavier dose of $N^{2+}$, while areas showing black indicate a lighter dose of $N^{2+}$. As the dose increases, the greyish silver will shine with metallic glow. This is an example of the first type photochromic material application.

The result of ion implantation map is an array of stable and repeatable measurements of work piece uniformity. The spectral shift information gives an insight of ion implantation mechanism, for example, implantation angle and duration, and distribution pattern. Device performance is strongly related to the result of ion implantation, and this work piece characteristics evaluation allows fine tune of the implantation process so as to achieve desirable ion distribution when the event occurs with actual semiconductor wafer.

The implanted work piece can be recycled after the data are recorded. A dominant advantage of photochromic material is owing to its reversibility. Spiropyrans, spirooxazines, diarylethenes, azobenzenes, poly[N,N'-(p,p'-oxydiphenylene)pyromellitimide (Kapton H) and 4-N, N-dimethylamino-4-N/-methyl-stilbazolium tosylate (DAST) are thermally reversible chemical species, although the back reaction takes place at different speed and condition. The thermal driven back reaction recovers the work piece to the first state, which is unimplanted. The substrate 230 is provided with sufficient heat to allow back reaction takes place, and the chemical species is altered from the second state to the first state. The recovered work piece can be used again for a new cycle of ion implantation and operation 110 can be skipped. The recovery may sometimes be a decoloration process depending upon the property of the chemical species.

In the case where the photosensitive material is not thermal reversible, for example, AgBr, the implanted work piece can still be recovered but through a different approach. When AgBr is used as the photosensitive layer 222, it is nearly transparent before ion implantation. The energetic ions excite the molecules, and AgBr turns into Ag and $Br_2$, which gives a darker shade. The colour alternation is the indicator of ion implantation pattern. AgBr transformation is irreversible, and the recovery of implanted work piece involves photosensitive layer removal. The implanted photosensitive layer removal requires polymer removal chemical, such as sulfuric peroxide mixture. Sulfuric peroxide mixture solution cleans residues off the substrate surface, and the substrate is ready for a complete new cycle of ion implantation evaluation process.

Figure 3:
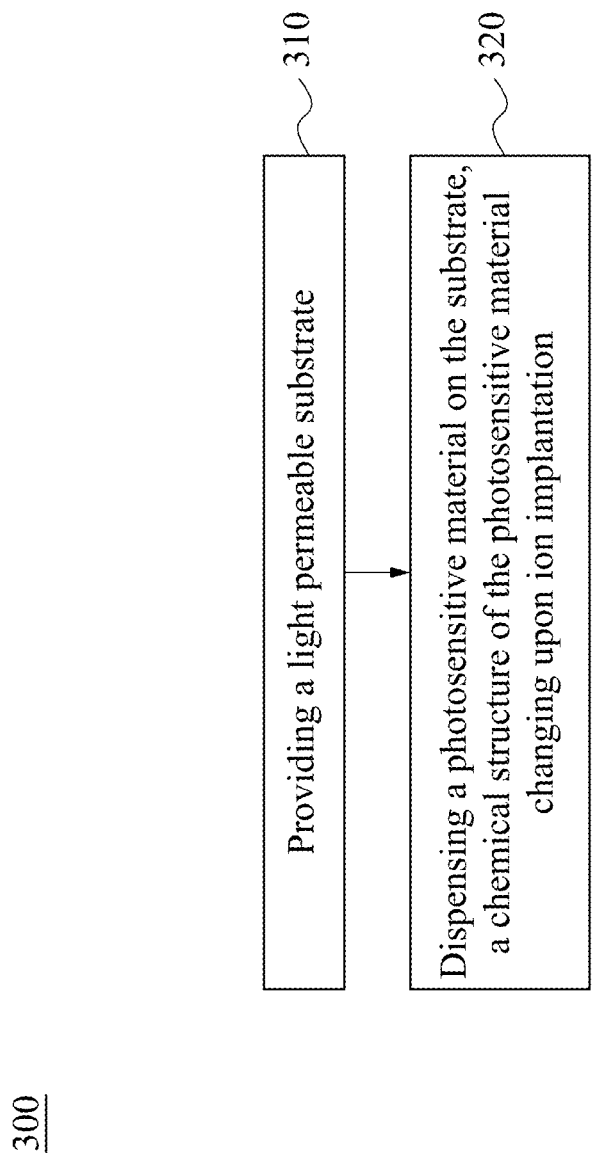
FIG. 3 is a flow chart showing a method of forming a photosensitive layer on a wafer sample in accordance with some embodiments of the instant disclosure.

Turning now to FIG. 3, illustrated is an embodiment of a method 300 for fabricating an ion implantation test work piece. As set forth in operation 310 in FIG. 3, a light permeable substrate is provided. The light permeable substrate may allow transmission of visible light. Visible light refers to light wavelength ranging between approximately 380 nm and 700 nm. This property allows colour transformation to be observed and recorded when chemical species responses to ion implantation. As set forth in operation 320 in FIG. 3, a photosensitive material is dispensed on the substrate to form a photosensitive layer on one surface of the substrate. The opposite surface of the substrate is free of the photosensitive layer. The selection of photosensitive material is similar to the photochromic materials described in the method 100. The photosensitive layer is responsive to electromagnetic excitement, and the chemical structure of the photosensitive material alters upon the stimuli. The electromagnetic excitement may involve ion implantation, UV exposure, high energy photon attacking or the like.

Photochromic phenomenon, for example, cis-trans isomerization, electrocyclic reactions, cycloaddition reactions, tautmerization and dissociation process, have real uses in ion implantation evaluation. The many important developments of photochromic pigments and material enable the application of mapping ion implantation. Conventional ion implantation measurement includes rapid thermal annealing, which contains uncertainties related to possible damage relaxation or incomplete anneal. In the instant disclosure, mapping of ion implantation is achieved by a photosensitive layer. The photosensitive layer contains chemical species, altering structure upon stimuli, such as ion implantation. The implanted ions causes chemical or physical property alternation of the chemical species, and colour transformation is predominately observed in the forward reaction. In addition, the forward reaction may involve physical property changes, for example, refractive index reduction or increase. These indicators are useful in interpreting the result of ion implantation. Furthermore, the implanted work piece can be recycled for a new test due to the reversibility of the photochromic material. Photosensitive layer may be made of photochromic material, and the key criterion of photochromic material is the ability to undergo forward and back reaction. Most photochromic material is thermal driven back, and this feature can be applied to an implanted work piece. The heated work piece recovers to unimplanted state and is ready for a new test. The instant disclosure provides a much faster evaluation process in the absence of rapid thermal annealing. The easy recycle of substrate also reduces evaluation time and cost.

In one embodiment of the instant disclosure, a method of evaluating an ion implanted work piece includes forming a photosensitive layer on the work piece. Then an ion implantation is performed on the work piece. The work piece is radiated, and an optical intensity of the work piece is calculated. The ion implantation pattern is evaluated according to the optical intensity.

In another embodiment of the instant disclosure, a test wafer work piece having modified surface is provided. The test wafer work piece includes a transparent substrate and a photosensitive layer disposed on the substrate. The photosensitive layer has photochromic materials, changing chemical structure upon ion implantation.

In still another embodiment of the instant disclosure, a method of forming photosensitive layer for testing is provided. The method includes providing a light permeable substrate and dispensing a photosensitive material on the substrate. A chemical structure of the photosensitive material changes upon ion implantation.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of evaluating characteristics of a work piece, the method comprising:
   forming a photosensitive layer on a substrate to form the work piece;
   performing ion implantation on the work piece;
   radiating the work piece; and
   calculating an optical intensity of the work piece based upon a transmission of light through the work piece from radiating the work piece.

2. The method of evaluating characteristics of a work piece according to claim 1, wherein performing ion implantation on the work piece further comprises:
   changing a chemical structure of the photosensitive layer.

3. The method of evaluating characteristics of a work piece according to claim 2, wherein calculating the optical intensity of the work piece further comprises:

measuring a refractive index difference of the photosensitive layer.

4. The method of evaluating characteristics of a work piece according to claim 2, further comprising:
recovering the chemical structure of the photosensitive layer by heat after calculating the optical intensity of the work piece.

5. The method of evaluating characteristics of a work piece according to claim 1, further comprising:
removing the photosensitive layer by a polymer removal chemical after calculating the optical intensity of the work piece.

6. The method of evaluating characteristics of a work piece according to claim 1, wherein:
radiating the work piece further comprises:
placing the work piece in between a light source and a meter matrix; and
receiving the optical intensity on the meter matrix, and
calculating the optical intensity of the work piece comprises:
transmitting the optical intensity to a processing unit; and
evaluating an ion implantation pattern according to the optical intensity.

7. The method of evaluating characteristics of a work piece according to claim 1, wherein the photosensitive layer comprises a photosensitive material selected from a group consisting of AgBr, spiropyrans, spirooxazines, diarylethenes, azobenzenes, poly[N,N'-(p,p'-oxydiphenylene)pyromellitimidel, 4-N, N-dimethylamino-4-N/-methyl-stilbazolium tosylate, and a combination thereof.

8. The method of evaluating characteristics of a work piece according to claim 1, wherein the work piece is a visible light permeable substrate.

9. An arrangement, comprising:
a transparent substrate;
a photosensitive layer disposed on the transparent substrate, wherein the photosensitive layer has a photochromic material configured to change chemical structure upon ion implantation;
a light shelter having a platform upon which the transparent substrate is seated; and
a meter matrix configured to measure optical intensity of light transmitted through the transparent substrate and the photosensitive layer.

10. The arrangement according to claim 9, wherein the transparent substrate is light permeable to wavelengths between 380 and 700 nm.

11. The arrangement according to claim 9, wherein the photochromic material is selected from a group consisting of AgBr, spiropyrans, spirooxazines, diarylethenes, azobenzenes, poly[N,N'-(p,p'-oxydiphenylene)pyromellitimidel, 4-N, N-dimethylamino-4-N/-methyl-stilbazolium tosylate, and a combination thereof.

12. The arrangement according to claim 9, wherein the chemical structure of the photosensitive layer is reversible by heat.

13. The arrangement according to claim 9, wherein a refractive index of the photosensitive layer is changeable.

14. The arrangement according to claim 10, wherein the light shelter extends from the platform to the meter matrix.

15. A method of evaluating characteristics of a work piece, the method comprising:
providing a light permeable substrate;
dispensing a photosensitive material on the light permeable substrate to form the work piece, wherein a chemical structure of the photosensitive material changes upon ion implantation;
performing ion implantation on the work piece;
radiating the work piece after performing the ion implantation on the work piece; and
calculating an optical intensity of the work piece based upon a transmission of light through the work piece from radiating the work piece.

16. The method of evaluating characteristics of a work piece according to claim 15, wherein dispensing the photosensitive material on the light permeable substrate is conducted under room temperature.

17. The method of evaluating characteristics of a work piece according to claim 15, wherein the light permeable substrate is permeable to wavelengths between 380 and 700 nm.

18. The method of evaluating characteristics of a work piece according to claim 15, wherein the light permeable substrate is a silicon wafer, silicon on insulation wafer, GaAs wafer, sapphire wafer or glass wafer.

19. The method of evaluating characteristics of a work piece according to claim 15, wherein a refractive index of the photosensitive material is changeable.

20. The method of evaluating characteristics of a work piece according to claim 15, wherein the photosensitive material is selected from a group consisting of AgBr, spiropyrans, spirooxazines, diarylethenes, azobenzenes, poly[N, N'-(p,p'-oxydiphenylene)pyromellitimidel, 4-N, N-dimethylamino-4-N/-methyl-stilbazolium tosylate, and a combination thereof.

* * * * *